United States Patent
Fouere et al.

(10) Patent No.: US 7,736,326 B2
(45) Date of Patent: Jun. 15, 2010

(54) LACHRYMAL PLUGS AND METHODS FOR SETTING SAME

(76) Inventors: Alain Fouere, "Le Thalassa", 120 rue du Commandant, Rolland, Marseilles (FR) 13008; Pierre Bige, 411 Chemin de Paramido, Saint-Cyr-sur-Mer (FR) 83270

( * ) Notice: Subject to any disclaimer, the term of this patent is extended or adjusted under 35 U.S.C. 154(b) by 810 days.

(21) Appl. No.: 10/787,170

(22) Filed: Feb. 27, 2004

(65) Prior Publication Data

US 2004/0210182 A1 Oct. 21, 2004

Related U.S. Application Data

(63) Continuation of application No. PCT/FR02/02878, filed on Aug. 14, 2002.

(30) Foreign Application Priority Data

Aug. 31, 2001 (FR) ................................ 01 11324

(51) Int. Cl.
*A61B 17/00* (2006.01)
*A61B 19/00* (2006.01)
(52) U.S. Cl. ................. 604/9; 604/8; 128/887
(58) Field of Classification Search .......... 604/8–10, 604/264, 19, 93.01, 500, 506, 540, 541, 48, 604/523, 514, 516; 606/106–108, 159, 160, 606/191, 196, 2, 4, 13–16; 128/897, 898, 128/887, 846; 607/80–89; 623/1.1, 1.11, 623/1.3, 1.31, 1.49, 23.7
See application file for complete search history.

(56) References Cited

U.S. PATENT DOCUMENTS

| | | | | |
|---|---|---|---|---|
| 3,949,750 A | * | 4/1976 | Freeman | 424/427 |
| 4,915,684 A | * | 4/1990 | MacKeen et al. | 604/8 |
| 4,959,048 A | * | 9/1990 | Seder et al. | 604/9 |
| 5,163,959 A | * | 11/1992 | Herrick | 128/898 |
| 5,334,137 A | | 8/1994 | Freeman | |
| 5,417,651 A | * | 5/1995 | Guena et al. | 604/8 |
| 5,830,171 A | | 11/1998 | Wallace | |
| 6,254,562 B1 | | 7/2001 | Fouere | |
| 6,629,533 B1 | * | 10/2003 | Webb et al. | 128/887 |

FOREIGN PATENT DOCUMENTS

WO 98/33461 8/1998

* cited by examiner

*Primary Examiner*—Leslie R Deak
(74) *Attorney, Agent, or Firm*—Greenblum & Bernstein, P.L.C.

(57) ABSTRACT

The invention concerns lachrymal plugs, and methods for setting said devices. It concerns a lachrymal plug (10) designed to be inserted in the lachrymal canaliculi (5), said plug, optionally provided with an axial duct, comprising on its outer walls flexible elements (11) foldable on said walls to enable the plug to be inserted in the lachrymal duct and adapted to straighten up once the lachrymal plug is set, so as to maintain the latter in position. The invention generally concerns means for controlling the flow of tears running from the surface of the eye towards the nasal cavity.

1 Claim, 2 Drawing Sheets

LACHRYMAL PLUGS AND METHODS FOR SETTING SAME

CROSS-REFERENCE TO RELATED APPLICATIONS

The instant application is a continuation of International Application No. PCT/FR02/02878 filed Aug. 14, 2002, the disclosure of which is expressly incorporated by reference herein in its entirety. Moreover, the instant application claims priority of French Patent Application No. 01/11324 filed Aug. 31, 2001.

BACKGROUND OF THE INVENTION

1. Field of the Invention

The present invention relates to lachrymal plugs and methods for positioning these devices.

The present invention is generally directed to controlling the flow of tears running from the surface of the eye towards the nasal cavity.

2. Discussion of Background Information

The normal functioning of the human eye requires that its outer surface be constantly covered with a lubricating film constituted by tears, that ensure both rinsing and protection due to the natural anti-infectious antibiotics that they contain. They are produced by a series of glands located in the eyelids and about the periphery of the eye.

The deficiency in maintaining the stability of this film on the eyeball can cause various nuisances, such as stinging, irritations, burning sensations and sight deterioration in the case of dryness on the eye surface.

Tears are produced continuously, the excess of fluid being drained from the eyeball surface 1 through two point openings constituting the upper 2 and lower 3 lachrymal points located near the inner corner of the eye and communicating with ducts known as canaliculi 4, 5, that lead to a lachrymal sac 6 that opens out into the nasal cavity 7. The lachrymal points 2, 3 are capable of opening or closing in the manner of a sphincter-type muscle, so as to ensure controlling the flow of the fluid (FIG. 1).

The lack of lachrymal fluid on the eyeball is generally due to a deficiency of the productive glands, which can be caused by age or by other factors.

It is possible to improve the situation by acting on the lachrymal ducts by completely or partially blocking them.

In particular, permanent blockage, possibly by surgery (cauterization, laser) of the lachrymal ducts, can be a method for treating tear-related deficiencies. When the flow of tears in the nasolachrymal sac is thus prevented, the volume of remaining tears generates greater moisture.

This method has the drawback of being irreversible, barring a new surgical intervention. To overcome this, removable devices capable of being positioned in a lachrymal duct and removed without surgical intervention have been proposed. For instance, U.S. Pat. No. 5,334,137, filed by "EAGLE VISION," describes a device for controlling the lachrymal fluid that blocks the flow of this fluid originating from the surface of the eye, and comprising an inverted truncated cone-shaped end portion and a head provided with a widened dome. The end portion is arranged to facilitate the positioning of the device through a point opening, and the widened dome prevents the complete penetration of the device into the vertical portion of the canaliculus through the point opening.

Nevertheless, this type of device has risks of accidental migration or expulsion. Furthermore, it requires a special apparatus for positioning and extraction, and it does not allow increasing the flow of the lachrymal fluid.

International Publication No. WO 98/33461, filed by Mr. Alain Fouéré, co-Applicant of the present application, describes a screwable meatus plug adapted to be implanted in the lachrymal points, and constituted of a substantially cylindrical body whose lateral surface comprises a helical threading, similar to that of a screw allowing to position it or remove it by screwing or unscrewing, the meatus plug comprising, or not, an axial through duct allowing the passage of a predetermined flow of lachrymal fluid.

However, this implant allows intervening only on the lachrymal points 2, 3, and not on the other parts of the tear flow system, such as the canaliculi 4, 5 (see FIG. 1).

Given their design, the dimensions of known systems must be adapted to the morphology of each patient, which requires a more or less wide range of prostheses of each type, resulting in an increase of the manufacturing and storing costs.

SUMMARY OF THE INVENTION

One aspect of the device according to the present invention, which is essentially adapted to allow the blockage of the lachrymal ducts, is to overcome these circumstances in order to fight against the disease, often called "dry eyes," by overcoming a deficiency of the lachrymal glands through the decrease or suppression of the flow of tears towards the nasal cavities.

This device, which is particularly easy to implant, has the advantage of being easily adapted to various morphologies of the lachrymal ducts, which allows using one size for all patients.

The present invention includes a lachrymal plug adapted to be inserted in the lachrymal canaliculi. This plug, possibly provided with an axial duct, comprises on its outer walls flexible elements that can be folded on the walls to allow for the insertion of the plug in the lachrymal duct, and the flexible elements are capable of being straightened once the lachrymal plug is set so as to maintain the latter in position.

One aspect of the present invention includes a lachrymal plug adapted essentially to allow the blockage of the lachrymal ducts to overcome a deficiency of the lachrymal glands by decreasing or suppressing the flow of tears toward the nasal cavities. This lachrymal plug is characterized in that it is constituted of a substantially cylindrical body, on the external lateral walls of which are implanted flexible elements, that can be applied against these walls to allow the insertion of the lachrymal plug in the lachrymal duct, and can straighten when they are released so as to maintain said lachrymal plug in position. Moreover, the flexible elements can be radial pins and the pins can be tilted in the direction of the nasal cavities, so that they cannot be displaced by the natural peristalsis of the lachrymal duct driving tears and foreign bodies inwardly. The pins can be of a constant length, the pins can be of a variable length, or the pins can be of an increasing or decreasing length. The pins can be arranged in helical formation around the body. Additionally, the lachrymal plug can include one or several elements, such as flexible disks, arranged to ensure its impermeability. Furthermore, the flexible elements can have sufficient elasticity to partially penetrate into the inner wall of the lachrymal canaliculus by straightening, so as to ensure that the lachrymal plug is firmly held in position. The lachrymal plug can further be provided with an axial duct allowing for a reduced passage of the tears. Moreover, the lachrymal plug can take the form of a cone, a double cone, or a diabolo. Additionally, the lachrymal plug can be made of metal. In particular, the lachrymal plug can be made of a shape memory metal. Furthermore, the lachrymal plug can include a radio-opaque reference, visible with X-rays, to facilitate the marking during its progression when it is positioned.

Another aspect of the present invention includes a method for positioning a lachrymal plug where the positioning is carried out through the use of a tube having a push rod, arranged to allow pressing the pins against the outer wall of the element and to release them once the prosthesis is in position. This method for positioning a lachrymal can further include positioning with an instrument provided with jaws, similar to those of a mechanical pencil. Moreover, the instrument can be arranged to also allow undertaking the removal of the prosthesis.

BRIEF DESCRIPTION OF THE DRAWINGS

On the attached drawings, given by way of non-limiting examples of embodiments according to the present application.

DETAILED DESCRIPTION OF THE PRESENT INVENTION

The device of the present invention shown in FIGS. 2-10, includes a substantially cylindrical body 10, on the outer lateral walls of which are implanted flexible elements such as radial pins 11 that can be applied or collapsed against the walls and straightened when released.

Figure 5:
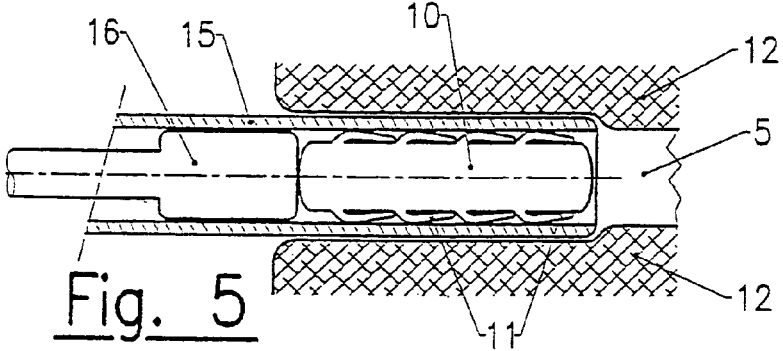
FIG. 5 is an axial cross-sectional view showing the positioning of a lachrymal plug with a tube having a push rod.

These flexible elements have a sufficient predetermined elasticity to partially penetrate into the inner wall 12 of the canaliculus 4, 5, by straightening up, so as to ensure that the lachrymal plug is firmly held in position as shown in FIG. 5.

Figure 1:
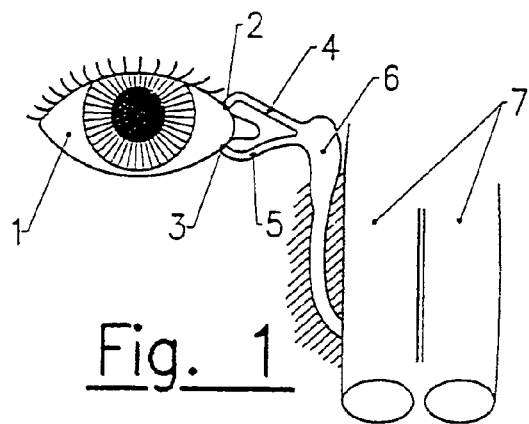
FIG. 1 schematically shows an eye with the lachrymal ducts and the lachrymal sac.
Figure 8:
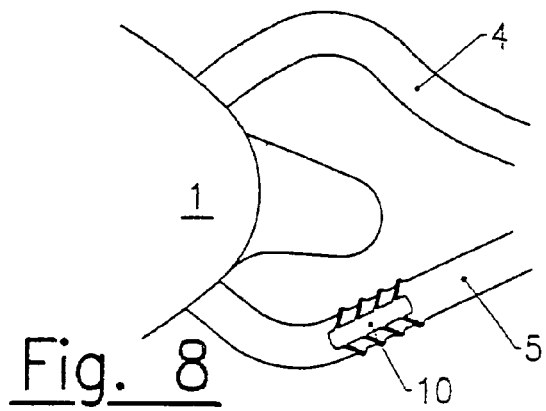
FIG. 8 shows a lachrymal plug according to FIG. 6 implanted in the lachrymal ducts.
Figure 2:
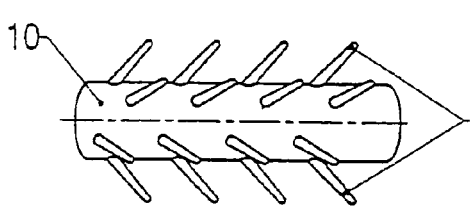
FIGS. 2 and 3 show a lachrymal plug according to the present invention seen from the side and end, respectively.
Figure 3:
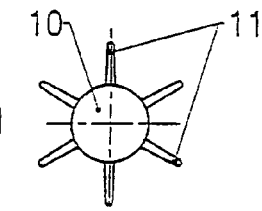
Figure 4:
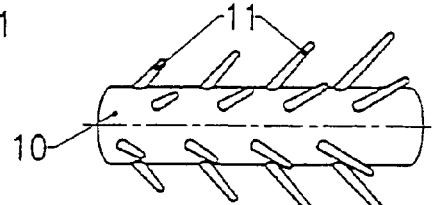
FIG. 4 shows an alternative of the lachrymal plug of FIGS. 2 and 3 provided with pins having an increasing length.
Figure 7:
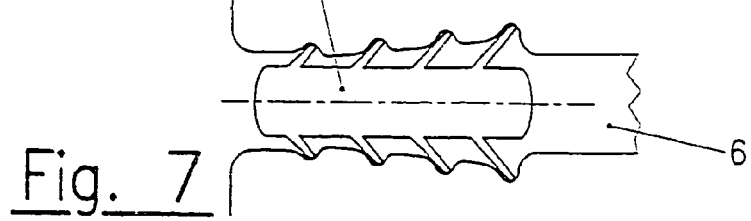
FIG. 7 shows an alternative of the lachrymal plug of FIG. 6, provided with pins having an increasing length.

The pins 11 can be arranged in helical formation or any other configuration. Their length can be constant, increasing as shown in FIGS. 4 and 7, decreasing or variable. They are advantageously tilted in the direction of the nasal cavities 7, so that they cannot be displaced by the natural peristalsis of the lachrymal duct which drives tears and foreign bodies inwardly.

Figure 9:
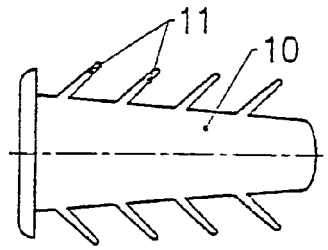
FIGS. 9-12 are axial cross-sectional views of three examples of possible forms of the device of the present invention.
Figure 6:
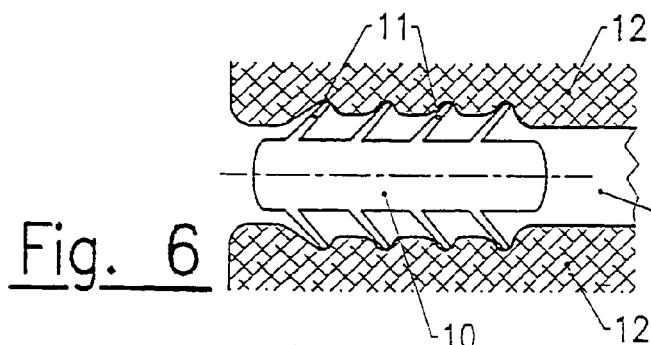
FIG. 6 shows, in the same conditions, the lachrymal plug once in position.

The exact shape of the body 10 can vary. For instance, it can have the form of a cone as shown in FIG. 9, a double cone as shown in FIG. 10, or even a diabolo, as shown in FIG. 11.

Figure 10:
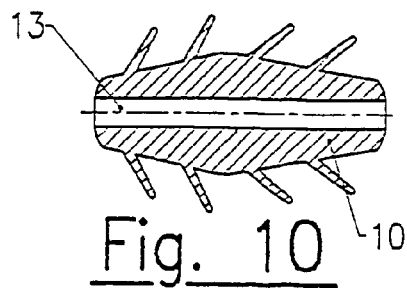
Figure 11:
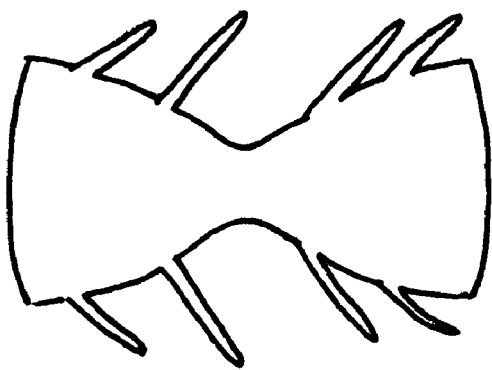

The body 10 can include an axial duct 13 allowing a reduced passage of the tears as shown in FIG. 10.

Figure 12:
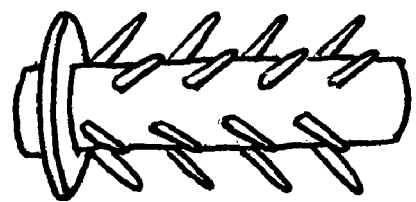

Furthermore, the device can advantageously further include at least one element, such as a flexible disk 12, arranged to ensure its impermeability, as shown in FIG. 12.

The lachrymal plug can be made of any material allowing the pins 11, or other flexible elements, to be folded and straightened. For example, the material can include metal or a synthetic material. In particular, it can be manufactured of a shape memory metal, offering the possibility of installing the lachrymal plug it without an instrument.

The lachrymal plug can also possibly comprise a radio-opaque reference, visible with X-rays, to facilitate the marking during the progression of the lachrymal plug when it is positioned.

The positioning of the lachrymal plug can be carried out by any known appropriate device that allows pressing the pins 11 against the outer wall of the body 10 of the lachrymal plug, and to release the pins once the lachrymal plug is positioned.

In particular, this device can include of a tube 15 having a push rod 16 as shown in FIG. 5, or of an instrument provided with jaws, similar to those of a mechanical pencil. Such an instrument would further be completely used for undertaking the removal of the prosthesis.

The positioning of the various elements gives the present invention a maximum of useful effects that, until now, had not been obtained by similar devices.

The invention claimed is:

1. A lachrymal plug that allows a blockage of the lachrymal ducts to overcome a deficiency of the lachrymal glands by decreasing or suppressing the flow of tears toward the nasal cavities, the lachrymal plug comprising:

a substantially cylindrical body having an external lateral wall; and flexible elements attached to the external wall structured and arranged to prevent migration so as to maintain said lachrymal plug in position, wherein the flexible elements comprise radial pins, and wherein the pins are arranged in helical formation around the body.

* * * * *